US008262222B2

(12) United States Patent
Levecq et al.

(10) Patent No.: US 8,262,222 B2
(45) Date of Patent: Sep. 11, 2012

(54) METHOD AND SYSTEM FOR CORRECTING ABERRATIONS OF THE EYE FOR AN OPHTHALMIC INSTRUMENT (75) Inventors: Xavier Jean-François Levecq, Gif sur Yvette (FR); Nicolas Chateau, Paris (FR)

(73) Assignee: Imagine Eyes, Orsay (FR)

( * ) Notice: Subject to any disclaimer, the term of this patent is extended or adjusted under 35 U.S.C. 154(b) by 721 days.

(21) Appl. No.: 12/064,065

(22) PCT Filed: Aug. 18, 2005

(86) PCT No.: PCT/FR2005/002098
§ 371 (c)(1),
(2), (4) Date: Jul. 11, 2008

(87) PCT Pub. No.: WO2007/020334
PCT Pub. Date: Feb. 22, 2007

(65) Prior Publication Data
US 2008/0309873 A1 Dec. 18, 2008

(51) Int. Cl.
*A61B 3/14* (2006.01)
*A61B 3/00* (2006.01)
(52) U.S. Cl. .................. 351/209; 351/205; 351/246
(58) Field of Classification Search .............. 351/205, 351/209, 246; 396/51
See application file for complete search history.

(56) References Cited

U.S. PATENT DOCUMENTS

| | | | |
|---|---|---|---|
| 4,856,891 A | 8/1989 | Pflibsen et al. | |
| 5,980,513 A | 11/1999 | Frey et al. | |
| 6,271,915 B1 | 8/2001 | Frey et al. | |
| 6,530,917 B1 * | 3/2003 | Seiler et al. | 606/5 |
| 6,601,956 B1 | 8/2003 | Jean et al. | |
| 6,610,049 B2 * | 8/2003 | Lai et al. | 606/5 |
| 6,923,802 B2 * | 8/2005 | Williams et al. | 606/5 |
| 7,281,797 B2 | 10/2007 | Yamaguchi et al. | |
| 2002/0013575 A1 * | 1/2002 | Lai et al. | 606/5 |
| 2002/0030789 A1 * | 3/2002 | Campin | 351/209 |
| 2003/0009156 A1 * | 1/2003 | Levine | 606/5 |
| 2003/0069566 A1 | 4/2003 | Williams et al. | |
| 2004/0160576 A1 * | 8/2004 | Lai et al. | 351/211 |
| 2004/0189941 A1 | 9/2004 | Bucourt et al. | |

FOREIGN PATENT DOCUMENTS

| | | |
|---|---|---|
| JP | 2005-506866 | 3/2005 |
| JP | 2006-006362 | 1/2006 |
| WO | WO 02/053020 A2 | 7/2002 |
| WO | WO 03/034909 | 5/2003 |
| WO | WO 03/105678 A2 | 12/2003 |

* cited by examiner

*Primary Examiner* — James Greece
(74) *Attorney, Agent, or Firm* — Greer, Burns & Crain, Ltd.

(57) ABSTRACT

A method for correcting aberrations of the eye applied to an ophthalmic instrument operating with an analysis light beam, including: measurement of aberrations of the eye capable of interfering with the analysis beam, correction of the phase of the wave front of the analysis beam as a function of the measured values of the aberrations, measurement of eye movements carried out independently of the measurement of aberrations, and modification of the correction of the phase of the wave front of the analysis beam as a function of the measurement of eye movements.

21 Claims, 8 Drawing Sheets

METHOD AND SYSTEM FOR CORRECTING ABERRATIONS OF THE EYE FOR AN OPHTHALMIC INSTRUMENT

The invention relates to a method and system for correcting a phase of a wave front of an analysis light beam as a function of measured values of aberrations of the eye for an ophthalmic instrument, as well as ophthalmic instruments equipped with such correction systems.

Ophthalmic instruments, such as for example instruments for retinal imaging or optical laser treatment on the retina operate with an analysis beam intended to pass through the various optical elements (cornea, crystalline lens etc.) from which the eye is formed, either as a beam incident on the eye (case of optical treatment of the retina), or as a beam emerging from the eye (case of retinal imaging). In all cases, the aberrations of the different optical elements of the eye cause aberrations of the wave front of the analysis beam, which degrades the quality of the optical instrument. Thus, in the case of retinal imaging, the image loses resolution and, in the case of the optical treatment of the eye, the quality of focussing of the laser on the retina is degraded. It is known to combine these ophthalmic instruments with a system for correcting aberrations of the eye making it possible to correct the wave front of the analysis beam, i.e. to give the optical beam phase the closest possible shape to a predetermined shape making it possible to obtain optimum performances from the instrument.

Such a system comprises, in a standard fashion, means for measuring aberrations of the eye, of Shack Hartmann analyzer type, and an optical device for correcting the phase of the wave front of the analysis beam, of deformable mirror type, or spatial light modulator type, controlled by means of a control unit for correcting the wave front as a function of the measured aberrations of the eye.

Such a system can also be used in a vision simulation type instrument, the purpose of which is to show a patient the effects of different corrections (ophthalmic lenses, contact lenses, optical treatment of the eye) by making him "see" an image, the analysis beam incident on the eye of the patient being then corrected for the ocular aberrations and/or effects induced by the phenomenon which it is desired to simulate.

However, the correction of aberrations of the eye is limited by the eye movements, lateral and axial movements or movements of rotation of the ocular axis, which induce variations in the aberrations of the eye at rapid frequencies of change (typically greater than 5 Hz). These variations in aberrations linked to ocular movements can be a particular nuisance in certain applications. In the case of retinal imaging for example, so-called "super resolution" retinal images are obtained by combining cross-section images of a very small field, originating from the same area of the retina. It is then necessary to have very good stabilization of the image of the retina on the image detector in order to carry out the combination, despite the rotational movements of the ocular axis. Similarly, in the case of optical treatment of the retina, lateral movements of the pupil as well as rotational movements of the ocular axis reduce the precision of the focussing of the laser on the retina.

The invention proposes a method for correcting aberrations of the eye as well as a system for the implementation of the method, making it possible to improve the quality of an ophthalmic instrument, based on an independent measurement of eye movement and taking this measurement into account in order to modify the correction of the aberrations.

More precisely, the invention relates to a method for correcting aberrations of the eye applied to an ophthalmic instrument operating with an analysis light beam, comprising:
measurement of aberrations of the eye capable of interfering with said analysis beam,
correction of the phase of the wave front of said analysis beam as a function of the measured values of said aberrations, characterized in that it also comprises:
measurement of eye movements carried out independently of said measurement of aberrations,
modification of the correction of the phase of the wave front of the analysis beam as a function of said measurement of eye movements.

The invention also relates to a correction system for the implementation of the method.

The method according to the invention also makes it possible in particular, thanks to the independent measurement of eye movements, to take into account the intrinsic aberrations of the eye (at a low frequency of change, typically less than 1 Hz), and variations in the aberrations linked to the eye movements, with a much more rapid frequency of change, in order to obtain a correction of the aberrations at a frequency at least equal to this frequency of change, without however working with a high frequency of the wave front analyzer, which would lead to an inevitable reduction in the spatial resolution of the analyzer.

Other advantages and characteristics of the invention will become more clearly apparent on reading the description, illustrated by the figures which follow.

In these figures, the identical elements are marked with the same references.

Figure 1:
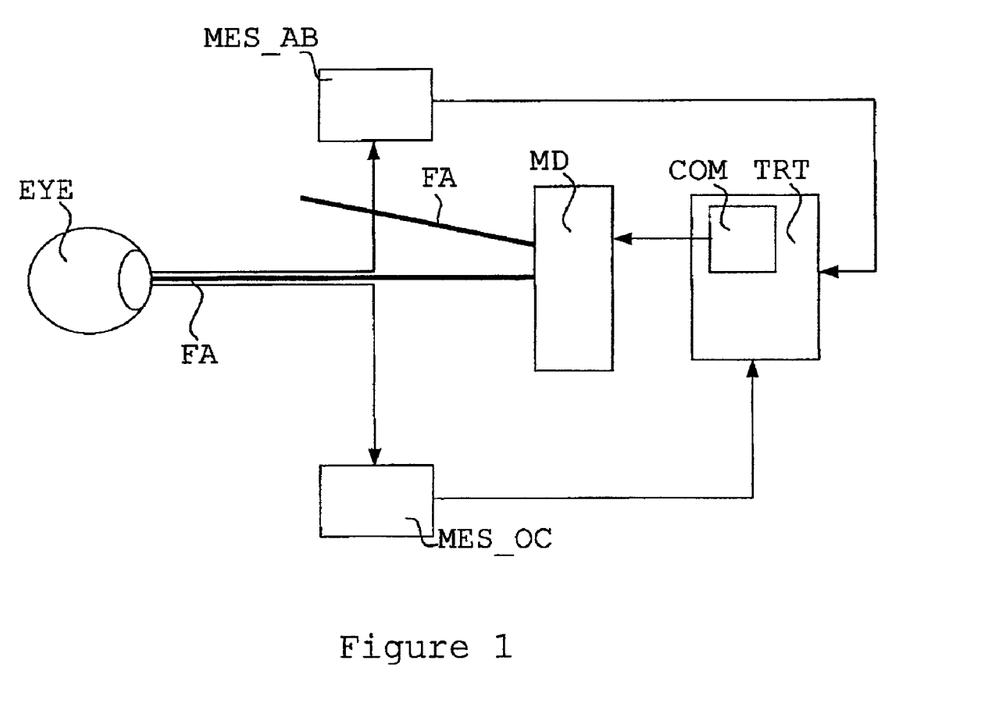
FIG. 1, a block diagram illustrating the correction system according to the invention.

FIG. 1 represents the block diagram of a correction system according to the invention, intended to be integrated into an ophthalmic instrument operating with an analysis light beam FA. In this figure the instrument itself is represented only by the analysis beam FA, symbolized in FIG. 1 by a bold line, either incident on the eye EYE of a patient (for example the case of optical laser treatment of the retina or the case of vision simulation), or emerging from the eye (the case of retinal imaging). The correction system comprises on the one hand means MES_AB for measuring aberrations of the eye which are capable of interfering with the analysis beam FA and an optical device MD for correcting the phase of the wave front of said analysis beam, as well as a control unit COM of the correction device with processing means TRT connected to the measurement means and calculating the correction values to be applied to the correction device as a function of the measured values of the aberrations. In FIG. 1, these elements are not represented according to an optical diagram but connected by arrows which indicate the functional connections between the elements. The correction system according to the invention also comprises a device MES_OC for measuring eye movements which is separate from the means for measuring aberrations, the eye movement measurement values being sent to the control unit in order to modify the correction of the phase of the wave front of the analysis beam. The performances of the ophthalmic instrument are improved thanks to the independent measurement of eye movements and the taking this measurement into account in order to modify the correction of the aberrations.

Figure 2A:
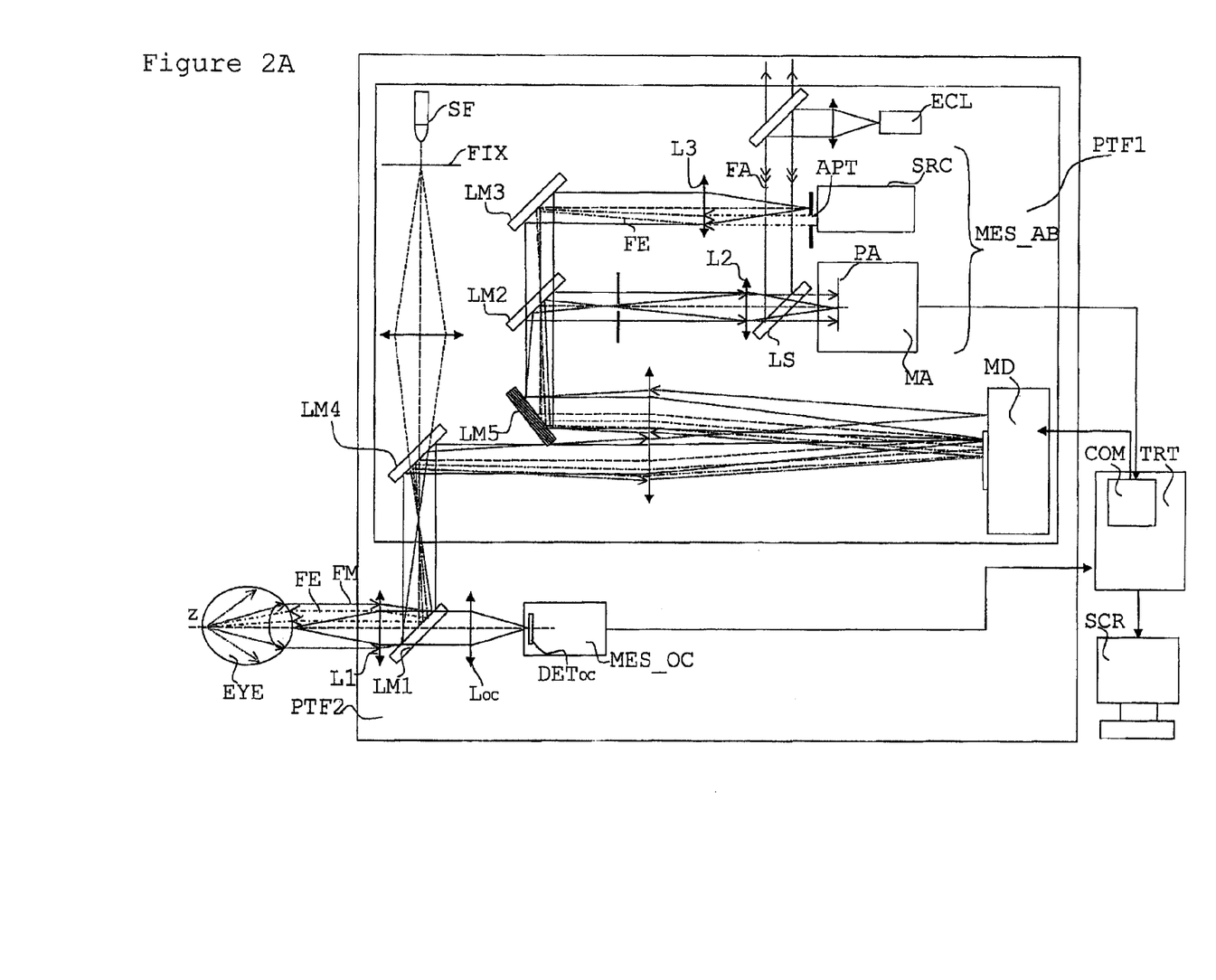
FIGS. 2A to 2C, diagrams of a retinal imaging type instrument or ocular treatment type instrument equipped with a correction system, according to different embodiment examples.
Figure 2B:
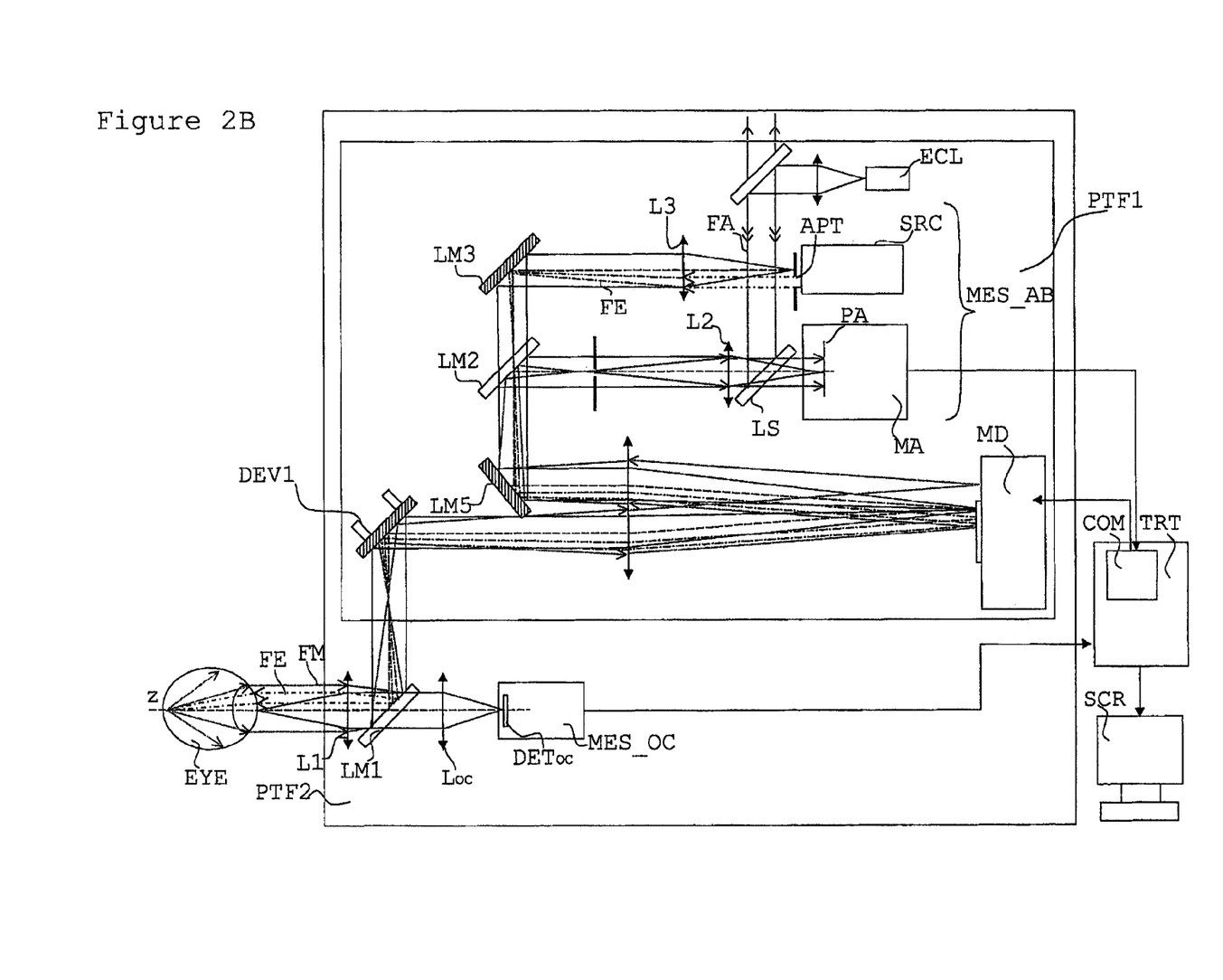
Figure 2C:
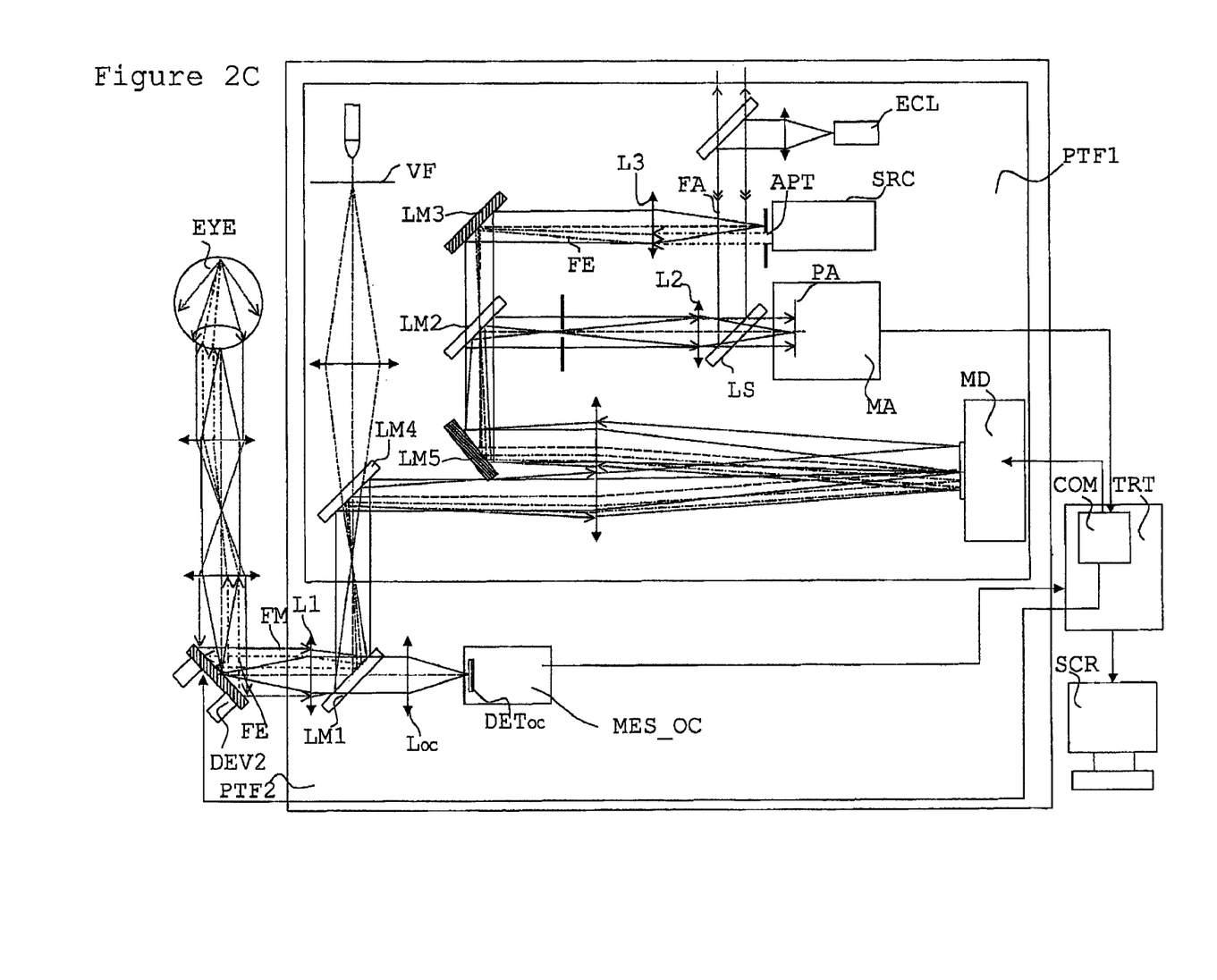

FIGS. 2A to 2C represent the optical diagrams of a retinal imaging type instrument or ocular treatment instrument equipped with a system for correcting aberrations of the eye according to the invention, in different embodiment examples. For the sake of clarity, these diagrams are not to scale. By retinal imaging system is meant any type of instrument allowing the visualization of the retina whatever its operating method. This can be for example a fundus oculi camera system, an angiography system, a Scanning Laser Opthalmoscope (SLO), or Optical Coherence Tomography (OCT) type instrument.

A retinal imaging instrument comprises in a standard manner a retina illumination system ECL making it possible to illuminate the retina over the area that is to be imaged, an imaging and detection system at the output of the retinal imaging instrument receiving an analysis beam FA, reflected back by the retina and emerging from the eye. In the example of FIG. 2A, the objective and the imaging detector are not shown. The intrinsic aberrations of the eye deform the wave front of the analysis beam and therefore reduce the resolution of the image. In a standard fashion, the retinal imaging instrument also comprises a system for correcting intrinsic aberrations with in particular means MES_AB for measuring aberrations of the eye, an optical device MD for correcting the phase of the wave front of the analysis beam making it possible to compensate for the measured aberrations, and a control unit COM of the correction device connected to measurement means and comprising processing means TRT making it possible to calculate the correction values to be applied as a function of the measured values of the aberrations.

A system for measuring the aberrations is described in the French patent application FR0111112. It comprises in particular an illumination path with, in particular, means SRC for the emission of an illumination beam FE (dash-dotted line in FIGS. 2A to 2C) and an illumination aperture APT for forming a diffusing point light source on the retina of the eye to be analyzed EYE. In the case of retinal imaging, the area illuminated by the illumination system ECL is typically ten times greater than the size of the light spot formed by the illumination beam FE, and an approximation is made that the aberrations measured at this point are slightly variable over all of the area illuminated by the illumination beam ECL. Advantageously, the wavelengths of the illumination beams FE and of the illumination system ECL are different in order to simplify the optical separation of the beams. It also comprises an analysis path with, in particular, optical analysis means MA in a given analysis plane PA of the phase of the wave front emitted by said point source and emerging from the eye (beam FM represented as dotted lines in FIGS. 2A to 2C). Imaging means L1 centred on a measurement axis z corresponding to the ocular axis in a given position of the eye, combined with imaging means L2 on the analysis path and L3 on the illumination path making it possible to ensure the optical conjugation between the pupil of the eye, the plane of the illumination aperture APT and the analysis plane PA of the analysis means MA. The beam splitter LM2 defines the analysis and illumination paths. In the example of FIG. 2A, a fixation path, coupled to the system by a beam splitter LM4, is also provided, making it possible to fix the attention of the patient whose eye is being analyzed. It comprises an illuminated image FIX and imaging means L4 ensuring the optical conjugation of the image with the retina, or regulated such that the image is seen with slight myopic defocusing in order to stimulate disaccommodation. In this example, the analysis, illumination and fixation paths are immovably attached one to the others and are positioned on a platform PTF1 that is mobile along the measurement axis (z) with respect to the imaging means L1 in order to ensure the optical conjugations between the different elements of the system as a function of the ametropia of the eye.

The analysis means, for example a Shack-Hartmann type analyzer, are connected to the processing means TRT, which, in a known manner, establish the phase cartography of the wave emerging from the eye and calculate the aberrations. A representation of this cartography can be displayed on a screen SCR. The correction system also comprises the correction device MD which intercepts the analysis beam FA and which, controlled by the control unit COM connected to the processing means, makes it possible to locally modify the phase of the wave front of the analysis beam FA as a function of the values of the aberrations measured by the measurement means MES_AB on the measurement beam FM. The analysis beam FA follows an optical path similar to that of the measurement beam FM thanks to the beam splitter LS which ensures a good coherence between the aberrations measured on the beam FM and the correction undergone by the beam FA. The optical correction device MD is formed for example by a deformable mirror constituted by a reflective surface which can be deformed by a set of actuators and on which the analysis beam is incident, substantially positioned in a plane conjugate with the pupil of the eye, each actuator being controlled by the control unit in order to correct the local phase of the wave front of the analysis beam. It is also possible to use a spatial light modulator (or SLM), for example produced by an array of liquid crystal valves. In FIGS. 2A to 2C, a beam splitter LS positioned on the analysis path sends part of the analysis beam FA after correction towards the objective and the retinal imaging detector.

However, these means are not sufficient to compensate for the aberrations resulting from the ocular movements the frequency of change of which is greater than the frequency of change of the intrinsic aberrations. These ocular movements, comprising lateral and/or axial displacements of the pupil and rotational movements of the ocular axis, on the one hand falsify correction of the aberrations, and on the other hand lead to inaccuracies in the focussing of the illumination beam on the retina. This latter effect is a particular nuisance for the formation of super-resolution images obtained by a combination of images originating from the same area of the retina.

The invention proposes a method for correcting aberrations of the eye making it possible to remedy the above-mentioned drawbacks and, more generally, to improve the quality of an ophthalmic instrument operating with an analysis light beam. The method for correcting aberrations of the eye according to the invention comprises, in addition to the measurement of aberrations of the eye and correction of the phase of the wave front of the analysis beam as a function of the measured values of said aberrations, the eye movement measurement carried out independently of said aberration measurement, and the modification of the correction of the phase of the wave front of the analysis beam as a function of said measurement of eye movements. The fact of carrying out an independent measurement of eye movements, i.e. in practice carried out by means different from those used for measuring the aberrations, makes it possible to supply the system with additional information, optionally at a more rapid frequency, and thus to obtain a more rapid correction of the eye movements, suited to the change in these movements.

The method is applied both to a continuous operation, in which the aberration measurement is carried out at a given recurrence frequency, and to pulsed or 'one shot' operation, in which it is sought to correct the system at given moments in time, for example in the case of laser shooting for the treatment of the retina. In the case where the aberration measurement is carried out continuously, at a given frequency, the modification of the correction can, by means of the invention, be carried out at an operating frequency strictly greater than the aberration measurement frequency. For example, the measurement of eye movements is itself carried out continuously, at a frequency strictly greater than the aberration measurement frequency, advantageously a multiple of said aberration measurement frequency, the operating frequency being able to be equal to the frequency of the measurement of eye movements, or even greater in the case, for example, where the measurement of eye movements is carried out with a time shift with respect to the aberration measurement. Typically, the aberration measurement frequency is comprised between a few Hertz and a few tens of Hertz, and the eye movement measurement frequency is of the order of one hundred Hertz, which finally allows a modification of the correction of the aberrations at a speed sufficient to take into account the eye movements and thus improve the quality of the instrument. In pulsed operation, the method for correcting the aberrations of the eye comprises in the same manner a phase of measurement of the optical aberrations of the eye by means of the wave front analyzer, a phase of measuring eye movements, then the calculation and the application of the modification of the correction to the correction element MD. The exploitation of the analysis beam FA is optimum at the instant when the correction element MD carries out the desired correction. When the aberrations to be corrected evolve rapidly, the shorter the time between the start and the end of the correction process, the better the result of the exploitation of the analysis beam. In this case, it is useful to synchronize the aberration measurement and ocular movement measurement phases in order to reduce as far as possible the overall measurement time. In certain applications, it is also possible to couple continuous operation phases and pulsed operation phases. In the case of pulsed operation, it is possible to extend the idea of frequency to the reciprocal of the duration of the measurement.

According to the invention, the measurement of eye movements can comprise estimation of the lateral and/or axial displacements of the pupil of the eye with respect to a predetermined position. In the case of an ophthalmic instrument having a sight axis which must be stabilized with respect to the ocular axis, the measurement of eye movements can also comprise estimation of the relative rotation of the axis of the eye with respect to a predetermined position. By sight axis is meant the direction towards which the instrument looks or aims, or the line which joins the centre of the entrance aperture of the instrument (which can be in a plane which coincides with that of the pupil of the eye) to the point at which the instrument is aimed or looking. The modification of the correction can then also be carried out as a function of the estimation of the rotation of the axis of the eye.

According to a variant, when the method according to the invention is applied to a retinal imaging instrument having a sight axis which must be stabilized with respect to the ocular axis, the measurement of eye movements can comprise, for each image of the retina taken, the estimation of the relative rotation of the axis of the eye with respect to a predetermined position, and the method can also comprise a subsequent stage of processing said images allowing the adjustment of the images as a function of the estimations of rotation of the sight axis.

FIG. 2A illustrates an example of a correction system according to the invention for the implementation of the correction method described above, making it possible to compensate for the effects of the ocular movements in the example of a retinal imaging instrument. For this purpose, it comprises a device MES_OC for measuring eye movements. This measuring device is separate from the means for measuring the aberrations MES_AB which makes it possible for it to analyze the variations in the ocular movements at a rapid given operating frequency, typically of the order of a hundred Hz, and in any case at least equal to the measurement frequency of the aberrations of the eye. The measurement device MES_OC, an embodiment example of which is described in detail hereafter, is positioned on the measurement axis z. The separation means LM1 make it possible to separate the path for measurement of the ocular movements from the other paths of the correction system, mounted on the platform PTF1. Advantageously, the platform PTF1, the imaging means L1 and the device MES_OC are positioned on a second mobile platform PTF2 in order to adjust the whole of the correction system to the positioning of the pupil of the eye.

The measuring device MES_OC makes it possible to estimate the displacements of the pupil of the eye with respect to a predetermined position. The displacement values are sent to the control unit COM in order to modify the correction of the phase of the wave front of the analysis beam with respect to the operating frequency. According to the invention, the modification of the correction can be carried out in several ways illustrated in FIGS. 2A and 2B. According to a first variant (FIG. 2A), new correction values are calculated by processing means TRT of the control unit of the correction device as a function of the measured values of displacement of the pupil. Then, the modification of the correction of the phase of the wave front is carried out by applying the new calculated correction values to the correction device MD, at the operating frequency of the measuring device MES_OC. According to another variant (FIG. 2B), an optical element DEV1 can be provided for deflecting the analysis beam, connected to the control unit, which makes it possible to stabilize, at the operating frequency, the position of the image of the pupil of the eye on the correction device MD as a function of the displacement values of the pupil. Advantageously, the optical element DEV1 is positioned in a plane close to a conjugated plane of the retina of the eye, which makes it possible in the retinal imaging application not to interfere with the formation of the image of the retina.

In a retinal imaging type application, or in any other application in which the ophthalmic instrument has a sight axis which it is desired to stabilize with respect to the ocular axis, the measuring device MES_OC also makes it possible to estimate the relative rotation of the axis of the eye with respect to a predetermined position. The rotation values are sent to the control unit in order to control, at the operating frequency of the measuring device MES_OC, the orientation of the instrument's line of sight. As previously, the orientation of the line of sight can be controlled by applying, at the operating frequency, new correction values calculated by the processing means of the control unit as a function of the measured rotation values of the axis of the eye. This requires the optical correction device MD, of deformable mirror type, to have a satisfactory operating dynamic.

According to a variant represented in FIG. 2C, it is also possible to provide an optical element DEV2 for deflecting the analysis beam, connected to the control unit, and making it possible to control, at the operating frequency, the orientation of the line of sight as a function of the relative rotation values of the axis of the eye. In this case, advantageously, the optical element is positioned in a plane close to a conjugated plane of the pupil of the eye, in order not to interfere with the correction of aberrations by modifying the position of the image of the pupil on the optical correction element.

The correction system according to the invention is also applied to an optical treatment instrument, an embodiment example of which is shown in the same FIG. 2A. The different paths of the correction system described previously are again found, namely illumination path, analysis path, fixation path and path of measurement of the ocular movements. Unlike the retinal imaging instrument, the ocular treatment instrument comprises a laser source (not specifically shown in FIG. 2A but which could take the place of the retina illumination source ECL) for emitting an analysis beam FA intended to be focussed on the retina of the eye along a given sight axis. In order to control the diameter and the shape of the laser spot formed on the retina, the instrument can be equipped with a standard correction system with the means MES_AB for measuring the aberrations of the eye, the optical device MD for correcting the phase of the wave front of the analysis beam and the control unit COM as described previously. The correction system according to the invention also makes it possible to adapt the correction as a function of the ocular movements with a rapid frequency compatible with the frequency of change of these movements, and to improve the precision of the position of the impact of the laser beam on the retina by means of a stabilization of the sight axis of the analysis beam FA with respect to the ocular axis, the variations in orientation of which are measured by the measuring device MES_OC.

Figure 3:
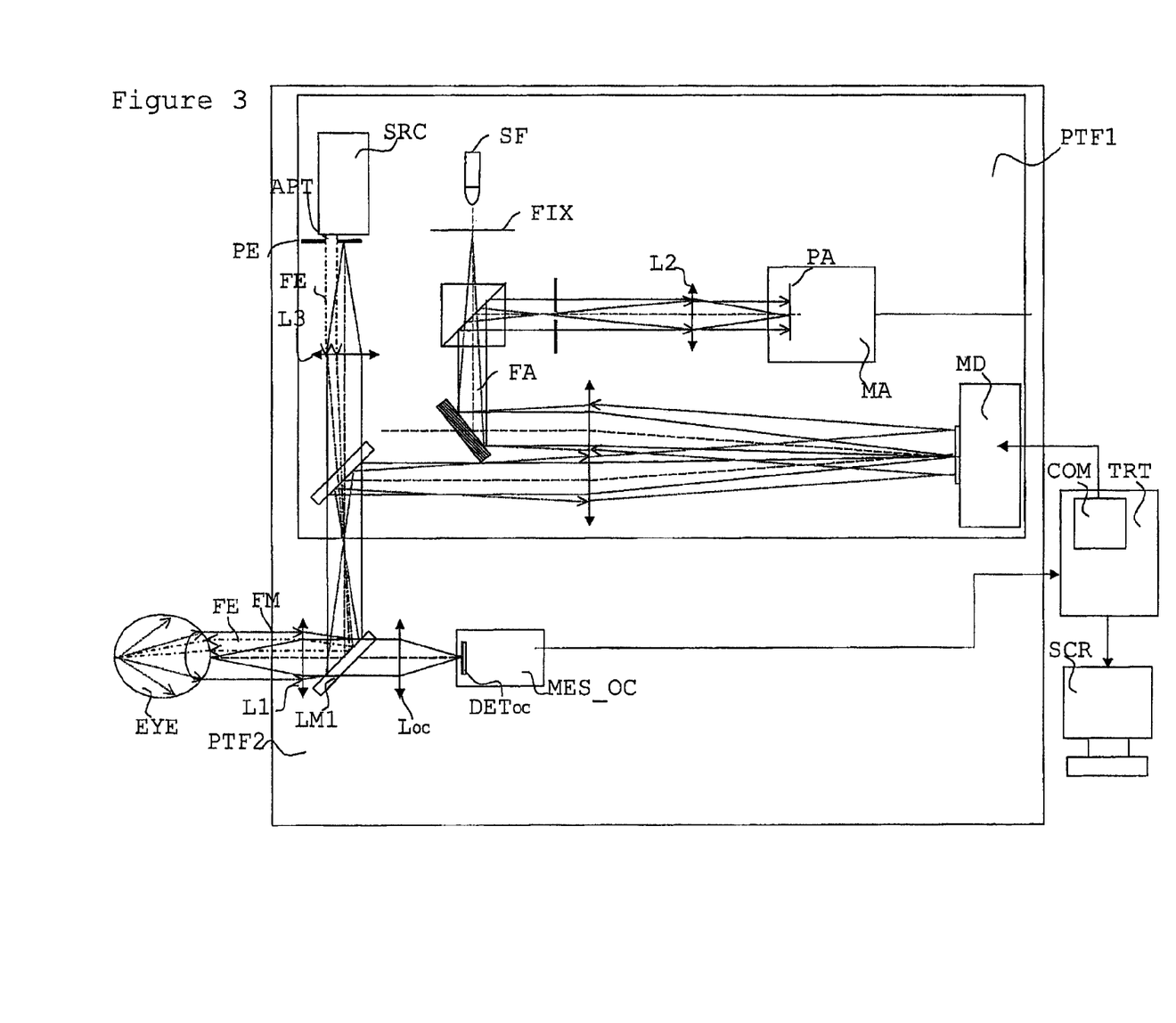
FIG. 3, the diagram of a vision simulation type instrument equipped with a correction system, according to an embodiment example.

FIG. 3 shows according to an example how the correction system according to the invention can be adapted just as well to a vision simulation type ophthalmic instrument used to simulate, to a patient, the image of a target which he could see with a given correction. Such an instrument comprises a fixation path similar to that described previously comprising a light source SF emitting an analysis beam FA and an image FIX illuminated by the analysis beam FA and intended to be seen by the patient. It comprises as previously means MES_AB for measuring the aberrations of the eye, an optical device MD for correcting the phase of the wave front of the analysis beam and a control unit COM. In this case, the processing means TRT of the control unit calculate as a function of the measured aberrations of the eye, to which are optionally added the effects of a correction by the ophthalmic lens, contact lens, etc. type, the corrections to be applied to the phase of the wave front of the analysis beam by the optical correction device MD. According to the invention, a correction system is provided to take account of the effects of the ocular movements in the calculation of the corrections to be applied to the phase of the wave front. As previously, it comprises a device for measuring ocular movements MES_OC making it possible to modify, at a frequency compatible with that of the ocular movements, the correction values of the phase of the wave front of the analysis beam as a function of the lateral movements of the pupil. There also, the modification can be made by calculation or by means of an optical deflection element.

Figure 4:
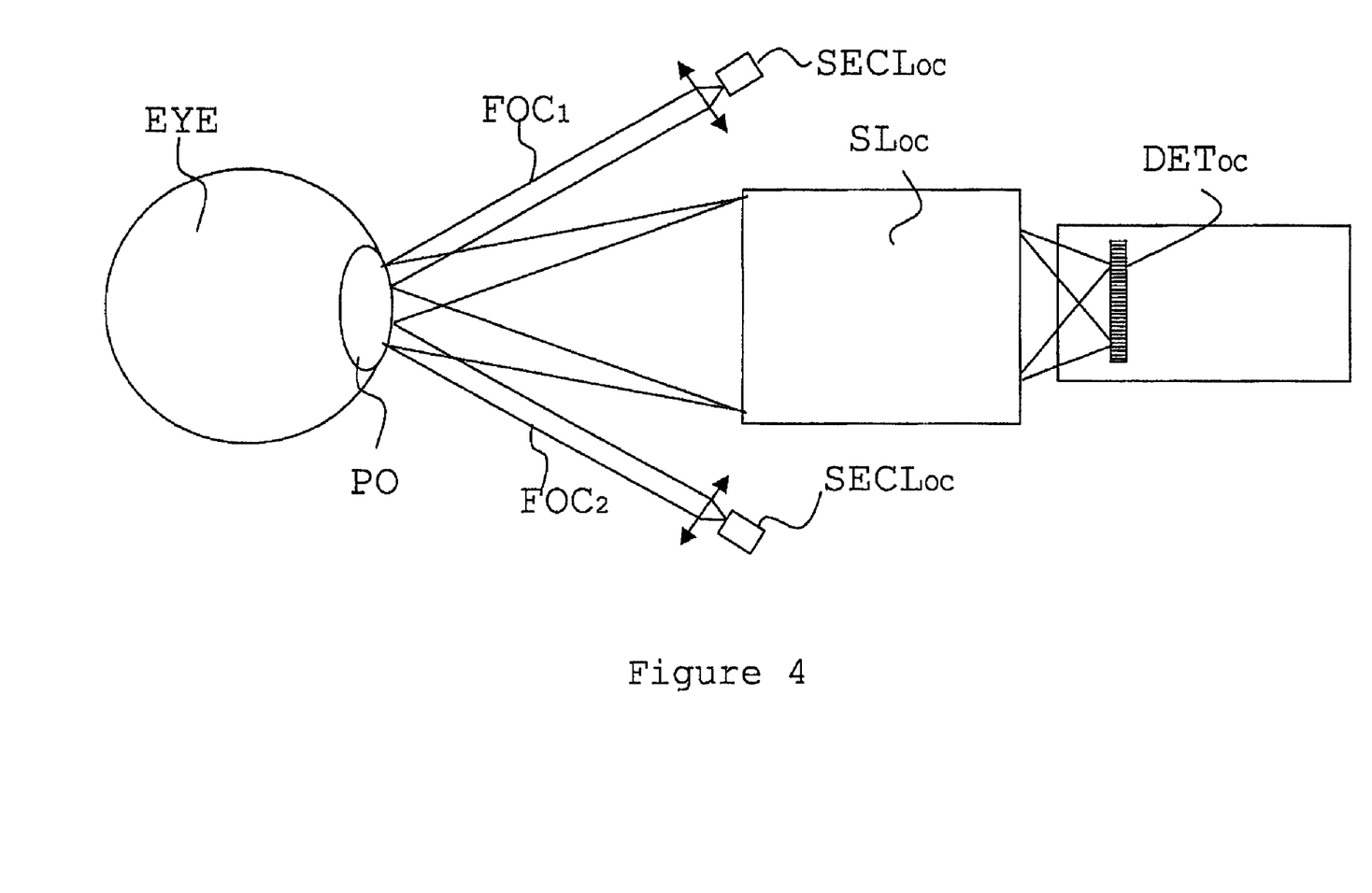
FIG. 4, an embodiment example of the device for measuring eye movements of the correction system according to the invention.

An embodiment example will now be described of the ocular movement measuring device of the correction system according to the invention using the example described in FIG. 4, the operation of which is made understandable by FIGS. 5A, 5B and 6. The device described in FIG. 4 is an optical-type device. Other devices can be envisaged, such as for example a device based on a detection of a magnetic field generated by contact lenses provided with induction coils. But an optical-type device, without contact, is preferred for the implementation of the invention. The device MES_OC for measuring eye movements comprises according to this example an array detector $DET_{OC}$, an objective $SL_{OC}$ forming the image IMA of the pupil PO of the eye EYE on the detector, illumination means $SECL_{OC}$ each emitting a substantially collimated beam $F_{OC1}$, $F_{OC2}$ incident on the pupil of the eye PO and forming two light spots on said pupil, processing means (not shown in FIG. 4), which can be the processing means TRT of FIGS. 2A to 2C, making it possible to determine the variations in the eye movements from the relative positions of the images T1, T2 formed by the objective $SL_{OC}$ of said spots with respect to the image IMA of the pupil.

Figure 5A:
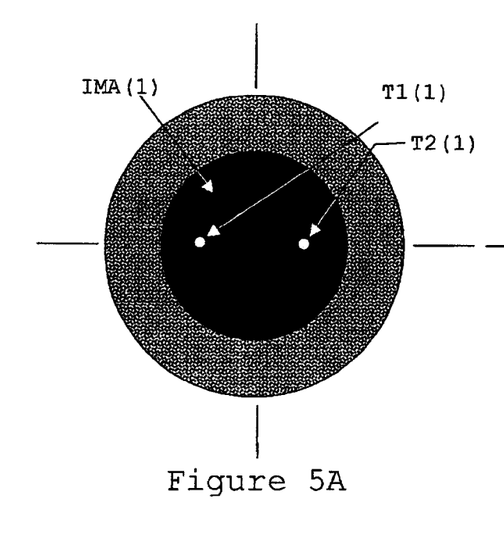
FIGS. 5A and 5B, images of the pupil formed by the measuring device of FIG. 4, according to two lateral positions of the eye.
Figure 5B:
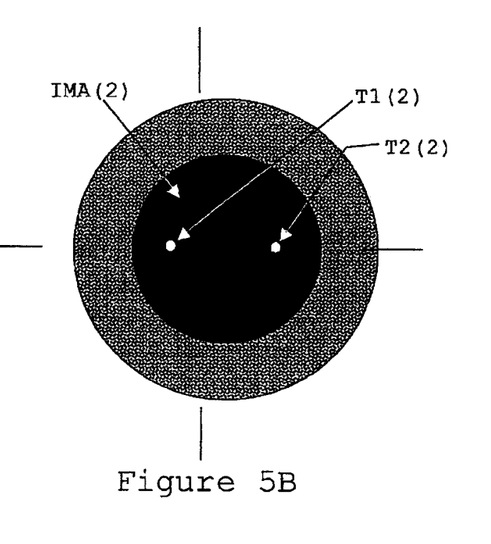

FIG. 5A represents the image of the pupil of the eye IMA (1) on the detector $DET_{OC}$ and the images T1(1), T2(1) of the two spots formed by the illumination means on the pupil in a first position of the patient's eye. In the case of a displacement of the head corresponding to a movement of pure translation, without rotation (without variation of the sight axis of the eye), given that the illumination beams are collimated, the image of the illumination sources by the cornea (equivalent to a convex mirror) is still in the same place in the reference frame of the cornea. In other words, a pure translation of the eye of a given value (without variation of the sight axis of the eye) leads, on the detector, to a translation of the same value of the image of the pupil and of the images of the sources by the cornea (known by the name Purkinje images). In FIG. 5B corresponding to a second position of the eye, an identical displacement of the image of the pupil IMA(2) and of the Purkinje images T2(1) and T2(2) are thus observed during a translation of the head of the patient.

Figure 6:
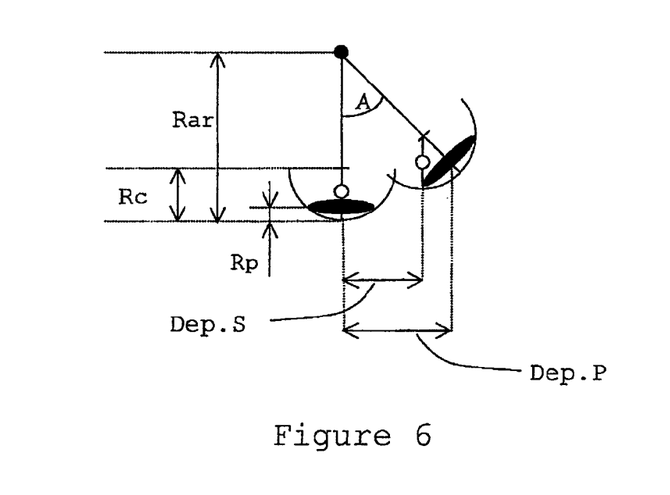
FIG. 6, a diagram illustrating the method for calculating rotation of the axis of the eye using the measuring device according to FIG. 4.

FIG. 6 illustrates the case of a variation in the orientation of the sight axis by an angle A with respect to the rotation axis of the eye (without movement of the head). The distance which separates the top of the cornea from the rotation axis of the eye is denoted Rar, the radius of curvature of the cornea is denoted Rc and the distance separating the top of the cornea and the image of the pupil by the cornea is denoted Rp. The following relations are verified:

$$Dep.P(\text{rot})=(Rar-Rp)*\sin(A)$$

$$Dep.S(\text{rot})=(Rar-Rc)*\sin(A)$$

Where Dep.P(rot) and Dep.S(rot) are respectively the displacements due to a movement of pure rotation, on the detector $DET_{OC}$, of the image of the pupil and the light source.

In the case of a movement both in translation and in rotation of the pupil of the eye, there is observed on the detector a displacement of the image of the pupil with a value of Dep.P (trans+rot) as well as a displacement of the images of the light sources of a displacement Dep.S(trans+rot). The displacement value of the image of the pupil Dep.P is processed by the processing means TRT in order to control the correction device MD with a view to modifying the corrections of the aberrations of the eye as a function of the lateral displacements of the pupil. The value for the variation of the sight axis of the eye is obtained:

$$Dep.P(\text{trans+rot})-Dep.S(\text{trans+rot})=(Rc-Rp)*\sin(A)$$

Rc can be easily measured by additional measurements (for example with a keratometer, or corneal topograph) and Rp can be measured by means of a tomography instrument. Thus the relation giving the value of angle A is the following:

$$A = a\sin((Dep.P(trans+rot) - Dep.S(trans+rot))/(Rc-Rp))$$

This value is sent if necessary to the control unit COM in order to obtain the stabilization of the sight axis of the analysis beam with respect to the ocular axis.

Figures 7A, 7C:
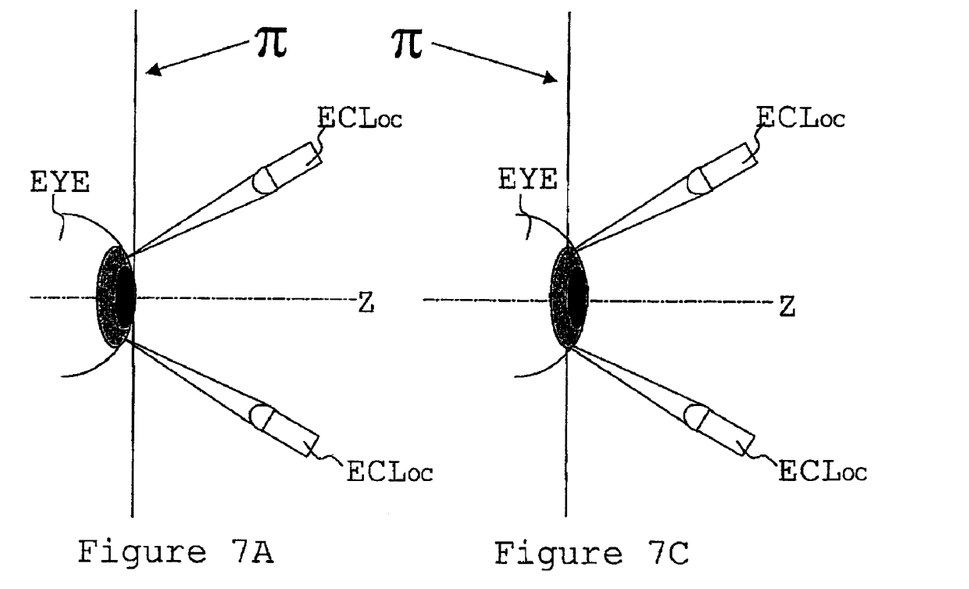
FIGS. 7A to 7D, diagrams illustrating the calculation of axial displacements of the pupil of the eye using the measuring device according to FIG. 4.
Figure 7B:
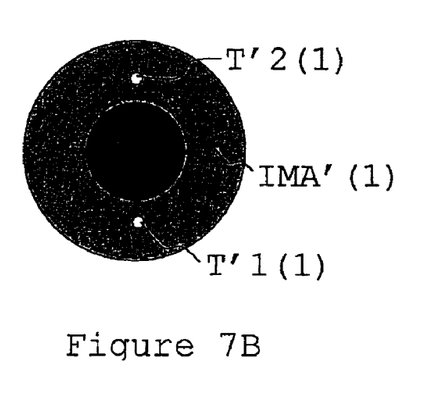
Figure 7D:
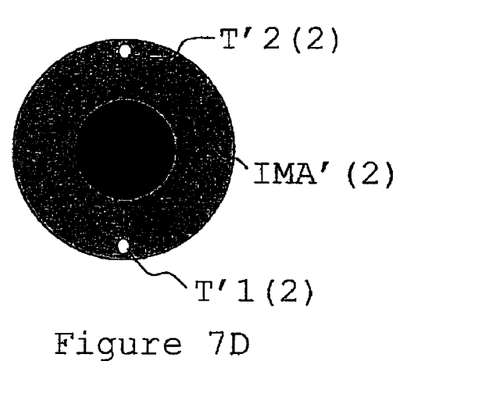

FIGS. 7A to 7D illustrate the principle of the measurement of axial displacements of the pupil of the eye by means of a device of the type of that described in FIG. 4 but in which the illumination system is different. For the measurement of axial displacements, the illumination system $ECL_{OC}$ comprises means for forming two point or virtually point light sources, along optical axes which are separate from each other and also separate from the sight axis z of the optical instrument, for example the retinal imaging instrument, on a diffusing part of the eye, the iris or the white of the eye. The images of these sources are observed by means of an imaging system and a detector of the type of those described in FIG. 4. The illumination system can use the same means as that described in FIG. 4 but adjusted differently, since in the case of the measurement of lateral displacements, the illumination system sends two substantially collimated beams. The space between the two images of the sources formed on the detector is proportional to the distance which separates the pupil of the eye from a given plane n, for example the best focussing plane. Thus FIG. 7A represents the patient's eye EYE in a first position with respect to the plane n and FIG. 7B represents the image IMA'(1) of the pupil of the eye EYE in this first position with the corresponding image of the point sources (T'1(1), T'2(1)) on the detector for measuring the ocular movements. FIG. 7C represents the patient's eye EYE in a second position with respect to the plane n and FIG. 7B represents the image IMA'(1) of the pupil of the eye EYE in this first position with the corresponding image of the point sources (T'1(2), T'2(2)). Measurement of the space between the two images of the sources makes it possible to deduce the axial displacement with respect to the reference plane n.

The invention claimed is:

1. A method for correcting aberrations of the eye by correcting a phase of a wave front of an analysis light beam as a function of measured aberrations of the eye, comprising:
measurement of aberrations of the eye capable of interfering with the analysis light beam,
correction of the phase of the wave front of the analysis light beam as a function of the measured aberrations,
measurement of eye movements carried out independently of said measured aberrations, and
modification of the correction of the phase of the wave front of the analysis light beam as a function of said measured eye movements,
wherein the aberration measurement is carried out at a given frequency and the modification of the correction of the phase of the wave front is carried out at an operating frequency greater than said aberration measurement frequency.

2. The correction method according to claim 1, in which said measurement of eye movements is carried out at a frequency strictly greater than said aberration measurement frequency, and that is a multiple of said aberration measurement frequency, the operating frequency being greater than or equal to the eye movement measurement frequency.

3. The correction method according to claim 1, in which the aberration measurement frequency is comprised between a few Hertz and a few tens of Hertz, and the eye movement measurement frequency is of the order of a hundred Hertz.

4. The correction method according to claim 1, in which the measurement of eye movements comprises a measurement of said movements carried out with a time shift with respect to said measurement of aberrations.

5. The method according to claim 1, in which the ophthalmic instrument having a sight axis which must be stabilized with respect to the ocular axis, the measurement of eye movements comprises the estimation of the relative rotation of the axis of the eye with respect to a predetermined position, and the modification of the correction is carried out as a function of said estimation of the rotation of the axis of the eye.

6. The method according to claim 1, in which said measurement of eye movements comprises the estimation of the lateral and/or axial displacements of the pupil of the eye with respect to a predetermined position.

7. The method according to claim 5, applied to a retinal imaging instrument having a sight axis which must be stabilized with respect to the ocular axis, in which the measurement of eye movements comprises for each image of the retina taken, the estimation of the relative rotation of the axis of the eye with respect to a predetermined position, and the method can also comprise a subsequent stage of processing of said images allowing the adjustment of the images as a function of the estimations of rotation of the sight axis.

8. A system for correcting aberrations of the eye by correcting a phase of a wave front of an analysis light beam as a function of measured aberrations of the eye, comprising:
means for measuring aberrations of the eye capable of interfering with said analysis light beam,
correction means including an optical device and a control unit, for correcting the phase of the wave front of said analysis light beam as a function of the measured aberrations, and
a device for measuring eye movements independently of said means for measuring the aberrations, said device for measuring eye movements comprising an array detector, an objective forming the image of the pupil of the eye on the detector, illumination means for forming two collimated beams incident on the pupil of the eye and forming two light spots on said pupil and processing means for determining variations in the eye movements from the relative positions of the spots with respect to the image of the pupil,
said control unit being arranged for modifying the correction of the phase of the wave front of the analysis light beam as a function of said measured eye movements.

9. The correction system according to claim 8, in which the device for measuring eye movements makes estimates at least one of the lateral and axial displacements of the pupil of the eye with respect to a predetermined position, said modification of the phase of the wave front is carried out by applying new correction values calculated by said processing means as a function of said displacement values of the pupil.

10. The correction system according to claim 8 in which, the device for measuring eye movements makes estimates at least one of the lateral and axial displacements of the pupil of the eye with respect to a predetermined position, the system also comprises a first optical element for deflecting the analysis light beam, positioned in a plane close to a conjugated plane of the retina of the eye, connected to the control unit, and making it possible to stabilize the position of the image of the pupil of the eye on the correction device as a function of said displacement values of the pupil.

11. The correction system according to claim 8 intended for an ophthalmic instrument having a sight axis which must be controlled with respect to the ocular axis, in which the device for measuring eye movements allows the estimation of the relative rotation of the axis of the eye with respect to a predetermined position, said rotation values being sent to the control unit in order to modify the correction of the phase of the wave front of the analysis light beam.

12. The correction system according to claim 11, in which the modification of the correction of the phase of the wave front of the analysis light beam is carried out by applying new correction values calculated by the control unit of the correction device as a function of the values of relative rotation of the axis of the eye.

13. The correction system according to claim 11, also comprising an optical element for deflecting the analysis light beam, positioned in a plane close to a conjugated plane of the pupil of the eye, connected to the control unit, and making it possible to control, at said operating frequency, the orientation of the line of sight as a function of said relative rotation values of the axis of the eye.

14. The correction system according to claim 8, in which the optical correction device is a deformable mirror constituted by a reflective surface which can be deformed by a set of actuators on which said analysis light beam is incident, substantially positioned in a conjugated plane of the pupil of the eye, each actuator being controlled by the control unit in order to correct the local phase of the wave front of the analysis light beam.

15. The correction system according to claim 8, in which the means for measuring aberrations of the eye comprise an illumination system with a source for emitting an illumination beam in order to form a secondary light source on the retina by backscattering, said secondary source emitting a measurement beam emerging from the eye, and means for analyzing the phase of the wave front of said measurement beam.

16. The correction system according to claim 15, in which the analysis means comprise a Shack-Hartmann type analyzer with an array detector, an array of microlenses receiving said measurement beam and forming on the array detector a set of light spots, and means for processing said light spots for determination of the aberrations.

17. A retinal imaging instrument comprising:
a retina illumination system emitting an illumination beam of given axis, an imaging and detection system receiving an analysis light beam emerging from the eye and carrying out the function of detection of the image of the retina on the detector of said imaging and detection system, and a system for correcting aberrations of the eye according to claim 11, allowing the correction of the phase of the wave front of the analysis light beam as a function of the estimation of the relative rotation of the axis of the eye with respect to a predetermined position.

18. An instrument for optical laser treatment on the retina comprising a laser source for the emission of an analysis light beam intended to be focused on the retina of the eye along a given sight axis, and a system for correcting aberrations of the eye according to claim 11, allowing the correction of the phase of the wave front of the analysis light beam as a function of the estimation of the relative rotation of the axis of the eye with respect to a predetermined position.

19. An instrument for simulation of the vision of a patient comprising a fixation system with a light source emitting an analysis light beam and a target illuminated by the analysis light beam and intended to be seen by the patient, and a system for correcting aberrations of the eye according to claim 8, allowing the correction of the phase of the wave front of the analysis light beam as a function of movements of the eye.

20. A retinal imaging instrument comprising: a retina illumination system emitting an illumination beam of given axis, an imaging and detection system receiving an analysis light beam emerging from the eye and carrying out the function of detection of the image of the retina on the detector of said imaging and detection system, and a system for correcting aberrations of the eye according to claim 8, allowing the correction of the phase of the wave front of the analysis light beam.

21. An instrument for optical laser treatment on the retina comprising a laser source for the emission of an analysis light beam intended to be focussed on the retina of the eye along a given sight axis, and a system for correcting aberrations of the eye according to claim 8, allowing the correction of the phase of the wave front of the analysis light beam.

* * * * *